United States Patent [19]

Bernhardt

[11] Patent Number: 5,375,478
[45] Date of Patent: Dec. 27, 1994

[54] TEST SAMPLE TAKING ARRANGEMENT
[75] Inventor: Bruno Bernhardt, Reutlingen, Germany
[73] Assignee: IEG Industrie-Engineering GmbH, Reutlingen-11-Betzingen, Germany
[21] Appl. No.: 922,809
[22] Filed: Jul. 30, 1992
[30] Foreign Application Priority Data Jul. 30, 1991 [DE] Germany .............. 4125141

[51] Int. Cl.$^5$ ............ E21B 49/08; G01N 1/14
[52] U.S. Cl. ............... 73/864.17; 73/155; 166/250
[58] Field of Search ........... 73/155, 864.16, 864.17, 73/864.18, 863.81, 863.82, 863.84, 863.86, 863.31; 166/250

[56] References Cited

U.S. PATENT DOCUMENTS

| | | | |
|---|---|---|---|
| 2,334,920 | 11/1943 | Gosline et al. | 73/155 |
| 2,609,878 | 9/1952 | Halliburton | 73/155 |
| 2,674,126 | 4/1954 | Coberly | 73/155 |
| 3,103,813 | 9/1963 | Bourne et al. | 73/155 |
| 3,283,570 | 11/1966 | Hodges | 73/155 |
| 3,454,085 | 7/1969 | Bostock | 73/155 |
| 3,472,070 | 10/1969 | Chenoweth | 73/155 |
| 3,908,454 | 9/1975 | Mullins et al. | 73/155 |
| 4,346,609 | 8/1982 | Diesel | 73/863.84 |
| 4,838,079 | 6/1989 | Harris | 73/155 |
| 5,186,048 | 2/1993 | Foster et al. | 73/155 |

FOREIGN PATENT DOCUMENTS

| | | |
|---|---|---|
| 3408595 | 9/1985 | Germany . |
| 3430130 | 2/1986 | Germany . |
| 3629870 | 3/1987 | Germany . |
| 3717594 | 12/1988 | Germany . |
| 3722653 | 1/1989 | Germany . |
| 2062581 | 11/1979 | United Kingdom . |

OTHER PUBLICATIONS

Water Resources Research, vol. 10, No. 2, p. 375 (Apr. 1974), "A Groundwater Profile Sampler", E. Hansen & A. Harris.

Primary Examiner—Hezron E. Williams
Assistant Examiner—George Dombroske
Attorney, Agent, or Firm—Michael J. Striker

[57] ABSTRACT

A test taking arrangement for several separate testing points, especially for ground water and ground air tests, the arrangement has a guiding tube insertable into a ground opening and having a wall which is gas and liquid permeable at least in regions of testing points, transverse walls arranged in the guiding tube between the regions of the testing points and provided with closeable openings for testing conduits and a cylinder-piston unit train, a cylinder-piston unit train having a plurality of coaxially arranged cylinder-piston units and piston rods, a joint drive device coupled with all the piston rods of all the cylinder-piston units of the cylinder-piston unit train, a plurality of suction conduits and pressure conduits, and an alternating valve to provide a connection of each cylinder chamber of the cylinder-piston unit train with a corresponding suction conduits ending in the region of a testing point and with a corresponding one of the pressure conduits leading to a corresponding sample taking point.

14 Claims, 2 Drawing Sheets

TEST SAMPLE TAKING ARRANGEMENT

BACKGROUND OF THE INVENTION

The present invention relates to a test sample taking arrangement for several test points separated front one another, particularly for ground water and ground air testing.

In arrangements for cleaning contaminated ground regions through negative pressure shafts provided in the contaminated ground region it is desirable, prior to or during the operation of the arrangement to determine the degree of contamination in different ground depths and this purpose to take samples from the regions of interest.

SUMMARY OF THE INVENTION

Accordingly, it is an object of the present invention to provide a test sample taking arrangement of this type, which is especially efficient and reliable in operation.

In keeping with these objects and with others which will become apparent hereinafter, one feature of the present invention resides, briefly stated, in a test sample taking device which has the following elements:

a) a guiding tube insertable into a ground region and provided with at least one gas and liquid permeable wall in the predetermined testing point regions;

b) transverse walls provided in the guiding tube between the individual testing point regions and having closeable openings for testing conduits and for a cylinder-piston unit train;

c) a cylinder-piston unit train assembled of several axially arranged cylinder-piston units, so that the piston rods of all cylinder-piston units are coupled with one another and with a joint drive device;

d) the connection of each cylinder-piston unit chamber of the cylinder-piston unit train via an alternating valve with a suction conduit ending in each testing point region and with a pressure conduit each leading to a specific sample taking point.

When the test sample taking arrangement is designed in accordance with the present invention, simultaneously samples can be taken along a rectilinear path in any regions or regions which are spaced from one another by corresponding distances. For the above mentioned preferable embodiment this testing path extends generally in a vertical direction, for example along a well tube in the filled ring chamber between the well tube and the shaft wall. It can also extend in different directions, for example in a horizontal direction. The tube serves not only for a coating of a provided (in particular drilled) ground opening, but also serves simultaneously for stabilizing the utilized cylinder-piston unit train which is supported via the transverse walls on the tube. The individual testing regions can be fixed in an accurate manner.

All cylinder-piston units of the cylinder-piston unit train are simultaneously actuated. They aspirate in the piston stroke direction the respective gas or liquid through the associated alternating valves in the individual testing point regions, and after the stroke reverse of the pistons displace the aspirated gases or liquids to individual pressure conduits which lead to a sample taking point. Due to the opposite-side coupling of their piston rods to an assembled joint piston rod of a corresponding joint drive device, simultaneously actuated cylinder-piston units can be coupled directly with one another, for example screwed. Instead, they can be combined to a cylinder-piston unit train in correspondence with the mutual distances between several testing point regions with a distance from one another and with spacer guiding tubes therebetween. The cylinder-piston units which are used here can be market available cylinder-piston units of corresponding size with one or several cylinder chambers. Also, market-available alternating valves can be used. The guiding tube insert can be withdrawn as a whole.

The guiding tube can be formed as a throughgoing gas and liquid permeable tube. Then the individual testing point regions can be separated from one another exclusively by the transverse walls arranged in the guiding tube. It is also possible to utilize a guiding tube which is only partially gas and liquid permeable, so that the individual testing point regions are separated not only by the inner transverse walls in the guiding tube, but instead also by impermeable guiding tube portions. In each case the guiding tube can be composed of individual portions, however with a step-free throughgoing inner wall.

It has been recognized that it is advantageous when the transverse walls are formed as piston-like wall bodies provided with peripheral sealing lips and anchored on the cylinder-piston unit train. Therefore they can be inserted into the guiding tube introduced in the ground opening, together with the cylinder-piston unit train. The cylinder-piston unit train can extend eccentrically through the transverse wall body. Thereby it is easier to arrange further pressure conduits which lead out of the guiding tube or suction conduits which lead to other testing regions through respective throughgoing openings in the transverse wall bodies.

The testing sample taking device in accordance with the present invention has the additional advantage that it can be easily adjusted to different testing conditions. It is possible to provide the joint drive device for the piston rods with a movement control device and/or an automatic control device for the piston rod stroke reverse. Therefore the actuation of the cylinder-piston units can be adjusted for example to the flow speed of the ground water at the testing points to avoid the formation of the pressure difference in the testing regions and to thereby prevent taking along of ground water or gas from neighboring ground regions in an undesirable manner. In the testing regions under pressure, during a long suction stroke of the arrangement, a slow post pumping of the ground water or gas into the increased cylinder chamber occurs without producing a negative pressure in the testing region. The danger of changing a sample due to the pressure changes is dispensed with. The guiding tube can also be used as support for additional device points, for example for the vibration generator. Such a vibration generator in accordance with the applicant's patent 3,931,012 is suitable for providing mechanical vibrations in limited ground regions for releasing molecular gas and/or liquid movements in the capillaries of the ground layers.

The arrangement in accordance with the present invention can also be used in open waters, and for this purpose the guiding tube is advantageously designed as a float. It can take water probes in the various water depths. So for example the oxygen content of the individual water layers for fish breeding can be controlled. Further advantage are obtained when the guiding tube, and in some cases also the spacer tubes between the cylinder-piston units, are made of permeable material, and a camera and/or other optical devices are arranged in the guiding tube for observation of the water flow.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
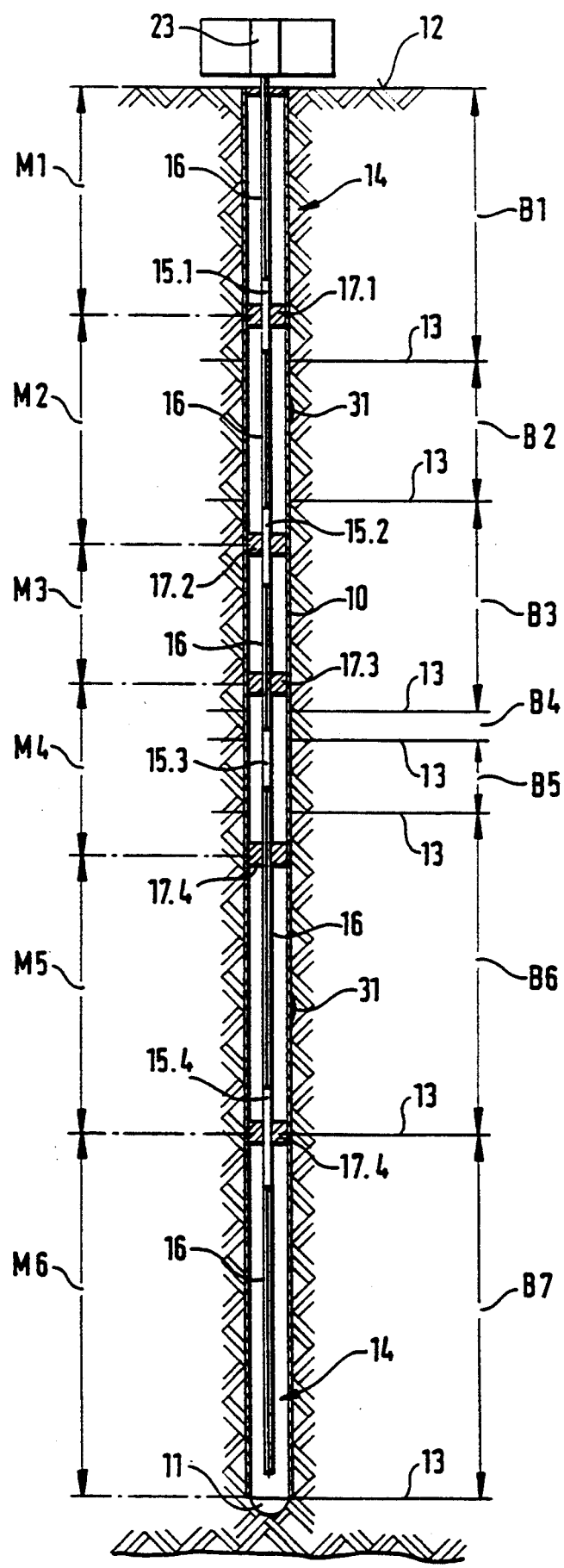
FIG. 1 is a view schematically showing a test sample taking arrangement in accordance with the present invention.

The arrangement for taking test samples has a circular cylindrical guiding tube which is identified with reference numeral 10 in FIG. 1 and inserted in a well opening 11. The well opening 11 extends from a ground region 12 through various ground layers B1–B7. The separating lines between the layers are identified with reference numerals 13. A cylinder-piston unit train 14 is inserted in the Guiding tube. In the shown example four cylinder-piston units 15.1–15.4 are provided and together with coaxial spacer tube 16 form the cylinder-piston unit train 14. Transverse walls 17.1–17.4 are anchored on the cylinder-piston unit train 14, preferably on cylinders 15 of the cylinder-piston units. The transverse walls subdivide the inner chamber of the Guiding tube into six testing regions M1–M6. Test samples of ground gas or ground water can be taken with the test sample taking arrangement simultaneously from each of the six testing regions M1–M6.

Figure 2:
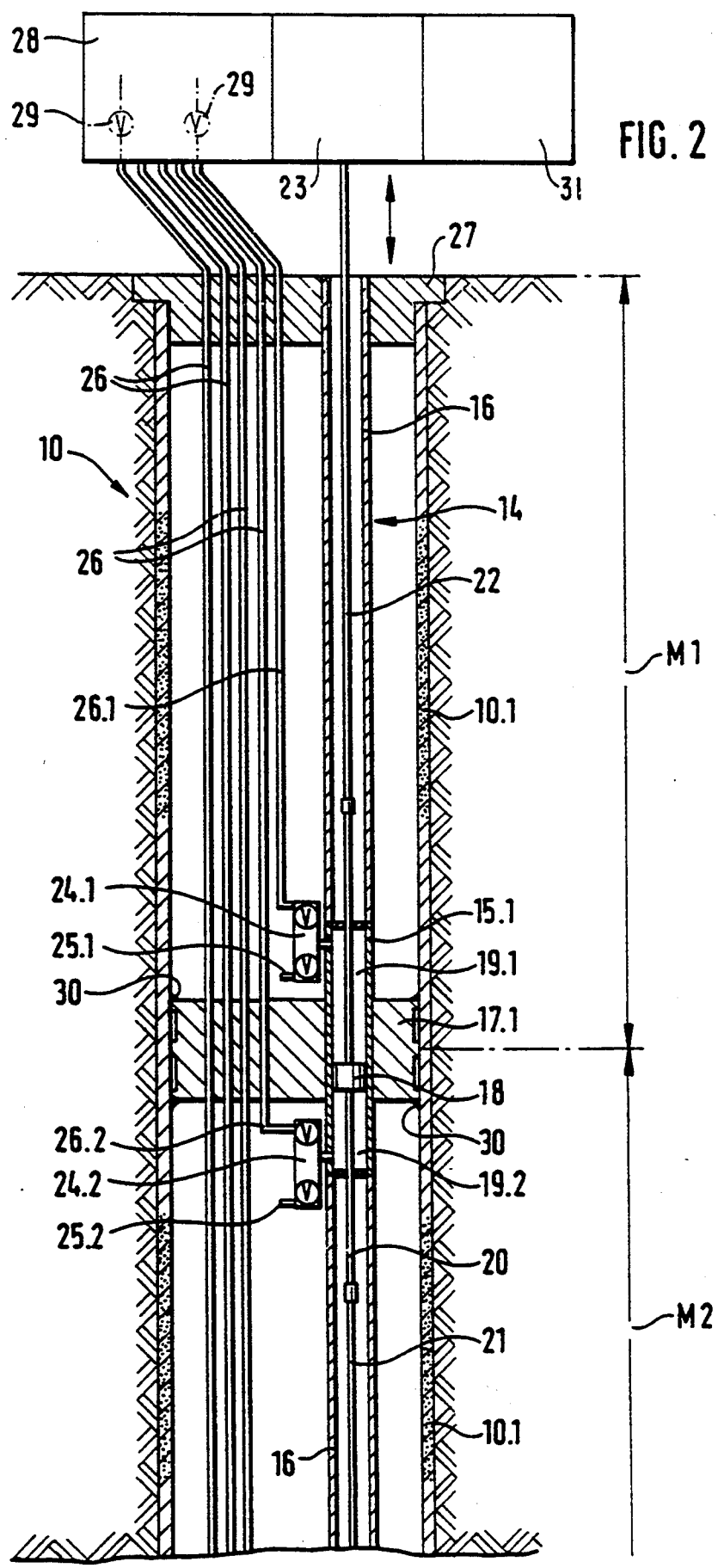
FIG. 2 is an enlarged view of an upper part of the the test sample taking arrangement in a central longitudinal section through the guiding pipe and the cylinder-piston unit train.

As can be seen from FIG. 2, the guiding tube 10 which can be assembled in a not shown manner from several tubular portions, has gas and liquid permeable wall portions 10.1. Such a permeable wall portion 10.1 is provided in each testing region M1–M6 shown in FIG. 1. Through these wall portions ground gases or ground water can penetrate from the neighboring ground layers B1–B7 into the interior of the guiding tube. The conventionally available intermediate chamber between the not shown well shaft wall and the outer wall of the inserted guiding tube 10 is filled in a not shown manner with a permeable material, such as gravel or coarse sand. Sealing layers from bentonite can be inserted in this filling in the region between the permeable wall portions 10.1 of the guiding tube. They prevent compensation streams between the individual testing regions along the wall of the guiding tube.

The cylinder-piston unit 15.1 arranged between two spacer tubes 16 has two cylinder chambers 19.1 and 19.2 which are separated from one another by a piston 18. The throughgoing piston rod 20 of the cylinder-piston arrangement is connected through a coaxial connecting rod 21 with the piston rod of the next cylinder-piston unit 15.2. Above, the throughgoing piston rod 20 is connected by a coupling rod 22 with a pneumatic, hydraulic, electro-motor or manually operating mechanical drive device 23. The pistons 18 of all cylinder-piston units 15.1–15.4 can be connected with the drive device 23 for providing a simultaneous movement upwardly or downwardly. The drive device 23 is provided with a device 31 for controlling the stroke speed and/or for an automatic change of the stroke direction.

Each of both cylinder chambers 19.1 and 19.2 is connected via an alternating valve 24.1 or 24.2 assembled from two one-way valves only of short suction conduits 25.1 or 25.2 on the one hand, and with a pressure conduit 26.1 or 26.2 on the other hand. The pressure conduits 26.1 and 26.2 which are shown only by thick lines and the corresponding pressure conduits 26 of another inserted cylinder-piston unit 15.2–15.4 are guided in the guiding pipe 10 through matching openings in the transverse walls 17 (for example 17.1) and an upper sealing cap 27 of the guiding tube, outwardly to a sample taking station 28. Throttle points 29 or pressure limiting elements can be inserted in the pressure conduits 26. The suction conduits 25 can lead also to another testing region.

The transverse walls 17 are formed as pistons with outer sealing lips 30 which can be seen on FIG. 2. The transverse wall 17.1 is arranged on the cylinder 15.1 so that the alternating valve 24.1 associated with the upper cylinder chamber 19.1 is associated with the uppermost testing region M1, and the alternating valve 24.2 connected with the lower cylinder chamber 19.2 is associated with the subsequent testing region M2. During the displacement movement of the coupling rod 22 and therefore the piston 18 in FIG. 2 upwardly, ground air, ground water or both are aspirated from the testing region M2 in the cylinder chamber 19.2 through the suction conduit 25.2 of the alternating valve 24.2. Simultaneously, the ground air, ground water or both aspirated from the upper cylinder chamber 19.1 into this cylinder chamber before is transported from the testing region M1 through the pressure conduit 26.1 in the sample taking point 28. During a downward movement of the piston 18 to the contrary the fluids are aspirated from the testing region M1 through the suction conduit 25.1 into the upper cylinder chamber 19.1 while the fluids aspirated before in the lower cylinder chamber 19.2 are transported from the testing region M2 through the alternating valve 24.2 into the pressure conduit 26.2 and high into the sample taking point 28.

The piston stroke movement is as a rule relatively slow in order to avoid excessively high negative pressure in the testing regions during aspiration of the ground air or the ground water in the individual testing regions. Otherwise, the testing results can be falsified. The pressure in each depth can be maintained. In FIG. 1 vibration generators 31 are arranged on the guiding tube 10. With the vibration generators mechanical vibrations of limited energy can be generated in respective ground regions B2 and B6 to release molecular gas and/or liquid movements in the capillaries of the bottom layers. As a result impurities can be taken from the capillary regions of the bottom layers into the testing regions M2 and M5.

The guiding tube 10 can be provided in its upper region with a not shown float, to use the arrangement for inspecting open waters. When the wall of the guiding tube 10 and the spacer tube 16 are composed of plexiglass, a camera for observation of the flow in the limiting water layers can be inserted in the guiding tube 10.

It will be understood that each of the elements described above, or two or more together, may also find a useful application in other types of constructions differing from the types described above.

While the invention has been illustrated and described as embodied in a test sample taking arrangement, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A sampling arrangement for several separate testing points, especially for ground water and ground air tests, the arrangement comprising a guiding tube insertable into a ground opening and having a wall which is gas and liquid permeable at least in regions of the testing points; transverse walls arranged in said guiding tube between the regions of the testing points and provided with openings for testing conduits and a cylinder-piston unit train having a plurality of coaxially arranged cylinder-piston units and piston rods, each of said cylinder-piston units of said cylinder-piston unit train being formed at least partially as a double chamber cylinder with two chambers each connected with another region of testing points; a joint drive device coupled with all said piston rods of all said cylinder-piston units of said cylinder-piston unit train for simultaneously moving said piston rods; a plurality of suction conduits and pressure conduits; two alternating valves to provide a connection of each cylinder chamber of said cylinder-piston unit train with two corresponding suction conduits ending in the region of a testing point and with two corresponding pressure conduits leading to a corresponding sample taking point; and a control device connected with said joint drive device and controlling the simultaneous movements of said piston rods by said joint drive device.

2. A sampling arrangement as defined in claim 1, wherein said transverse walls are formed as wall bodies which are provided with peripheral sealing lips and tightly adjusted to said guiding tube.

3. A sampling arrangement as defined in claim 1, wherein said transverse walls are connected with said cylinder-piston unit train.

4. A sampling arrangement as defined in claim 1; and further comprising axial spacer tubes arranged in said cylinder-piston unit train between said individual cylinder-piston units.

5. A sampling arrangement as defined in claim 1, wherein said cylinder-piston unit train is arranged eccentrically in said guiding tube.

6. A sampling arrangement as defined in claim 1 wherein said pressure conduits are provided with throttle points.

7. A sampling arrangement as defined in claim 1; and further comprising a float arranged on said guiding tube for utilization in open waters.

8. A sampling arrangement as defined in claim 1, wherein said guiding tube is composed of a transparent material; and further comprising an optical device inserted in said guiding tube for observing a water flow.

9. A sampling arrangement as defined in claim 8, wherein said optical device comprises a camera.

10. A sampling arrangement as defined in claim 1; and further comprising spacer tubes arranged between said cylinder-piston units of said cylinder-piston unit train, said spacer tubes being composed of a transparent material.

11. A sampling arrangement as defined in claim 1, wherein said control device is formed so as to control a stroke speed of movement of said piston rods by said drive device.

12. A sampling arrangement as defined in claim 1, wherein said control is formed so as to automatically change a stroke direction of said piston rods by said joint drive device.

13. A sampling arrangement for several separate testing points, especially for ground water and ground air tests, the arrangement comprising a guiding tube insertable into a ground opening and having a wall which is gas and liquid permeable at least in regions of the testing points; transverse walls arranged in said guiding tube between the regions of the testing points and provided with openings for testing conduits and a cylinder-piston unit train having a plurality of coaxially arranged cylinder-piston units and piston rods; a joint drive device coupled with all said piston rods of all said cylinder-piston units of said cylinder-piston unit train; a plurality of suction conduits and pressure conduits; an alternating valve to provide a connection of each cylinder chamber of said cylinder-piston unit train with a corresponding one of said suction conduits ending in the region of a testing points and with a corresponding one of said pressure conduits leading to a corresponding sample taking point; and at least one vibration generator arranged on said guiding tube and generating mechanical vibrations of limited energy in a neighboring ground region to release molecular gas and to provide liquid movements in capillaries of ground layers.

14. A sampling arrangement for several separate testing points, especially for ground water and ground air tests, the arrangement comprising a guiding tube insertable into a ground opening and having a wall which is gas and liquid permeable at least in regions of the testing points; transverse walls arranged in said guiding tube between the regions of the testing points and provided with openings for testing conduits and a cylinder-piston unit train having a plurality of coaxially arranged cylinder-piston units and piston rods, each of said cylinder-piston units of said cylinder-piston unit train being formed at least partially as a double chamber cylinder with two chambers each connected with another region of testing points; a joint drive device coupled with all said piston rods of all said cylinder-piston units of said cylinder-piston unit train for simultaneously moving said piston rods; a plurality of suction conduits and pressure conduits: and two alternating valves to provide a connection of each cylinder chamber of said cylinder-piston unit train with two corresponding suction conduits ending in the region of a testing point and with two corresponding pressure conduits leading to a corresponding sample taking point.

* * * * *